(12) United States Patent
Martin et al.

(10) Patent No.: US 6,933,149 B2
(45) Date of Patent: Aug. 23, 2005

(54) CULTURE SYSTEM FOR MOUSE TRACHEAL EPITHELIAL CELLS

(75) Inventors: Linda D. Martin, Apex, NC (US); Kenneth B. Adler, Raleigh, NC (US); Mariangela Macchione, São Paulo (BR); Nancy J. Akley, Raleigh, NC (US); Shaun A. McKane, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 43 days.

(21) Appl. No.: 10/132,680

(22) Filed: Apr. 25, 2002

(65) Prior Publication Data

US 2002/0197715 A1 Dec. 26, 2002

Related U.S. Application Data

(60) Provisional application No. 60/287,638, filed on Apr. 30, 2001.

(51) Int. Cl.[7] .................................................. C12N 5/06
(52) U.S. Cl. ........................................ 435/377; 435/354
(58) Field of Search ................................ 435/377, 354, 435/225, 347, 401, 402, 325

(56) References Cited

U.S. PATENT DOCUMENTS

| | | |
|---|---|---|
| 4,885,238 A | 12/1989 | Reddel et al. |
| 5,364,785 A | 11/1994 | Mather et al. |
| 5,667,766 A | 9/1997 | Wilson et al. |

OTHER PUBLICATIONS

Davidson et al., Am. J. Physiol. Lung Cell. Mol. Physiol., 279: L766–L778, 2000.*
Booth et al., Am. J. Respir. Cell Mol. Biol. 25: 739–743, 2001.*
Wu et al., Eur. Respir. J., 10: 2398–2403, 1997.*
Adler et al., Am. J. Respir. Cell Mol. Biol. 2: 145–154, 1990.*
Aliman et al., "Muc–5/5ac Mucin Messenger RNA and Protein Expression is a Marker of Goblet Cell Metaplasia in Murine Airways," 22 No. 3, pp. 253–260 (Mar. 2000).
Davidson et al., "A Primary Culture Model of Differentiated Murine Tracheal Epithelium" *Am. J. Physiol* 279 L766–778 (2000).
Fischer et al., "Tumor Necrosis Factor–alpha Stimulates Mucin Secretion And Cyclic GMP Production by Guinea Pig Tracheal Epithelial Cells In Vitro," *American Journal of Respiratory Cell And Molecular Biology*, American Lung Association 20 No. 3, pp. 413–422 (1999).
Guzman et al., "Epidermal Growth Factor Regulates Expression Of The Mucous Phenotype of Rat Tracheal Epithelial Cells," *Biochemical and Biophysical Research Communications*, Academic Press, Inc. 217 No. 2, pp. 412–418 (1995).

Kumar et al. Serum–free Culture of Mouse Tracheal Epithelial Cells *Experimental Lung Research* 23, No. 5, pp. 427–440 (1997).
Martin et al., "Secretion–competent Mouse Tracheal Epithelial Cell Culture From The Genetically Altered Mouse: Pathway Analysis via Gene Array," *CHEST* 121, No. 3, Suppl., p. 79S (Mar. 2002–2003).
Takacs–Jarrett et al., "Generation and Phenotype of Cell Lines Derived From CF and non–CF Mice that Carry the H–2K$^b$–tsA58 Transgene" *Am. J. Cell Physiol.* 280, C228–236 (2001).
Supplemental Partial European Search Report, EP 02 73 1491 mailed May 4, 2004.
Booth et al., *Interleukin–13 Induces Proliferation of Human Airways Epithelial Cells In Vitro via a Mechanism Mediated by Transforming Growth Factor–α, Am. J. Respir. Cell Mol. Biol.*, vol. 25, 2001. pp. 739–743.
Davidson et al., *A primary culture model of differentiated murine tracheal epithelium*, Am. J. Physiol Lung Cell Mol Physiol, vol. 279, 2000, pp. L766–L778.
International Search Report, PCT/US02/13019, Sep. 5, 2002.
Kim et al., *Airway Mucus*, Eur. Respir. J., vol. 10, 1997, p. 1438.
Krunkosky et al., *Effects of TNF–α on Expression of ICAM–1 in Human Airway Epithelial Cells In Vitro*, American Journal of Respiratory Cell and Molecular Biology, vol. 22, 2000, pp. 685–692.
Li et al., MARCKS *Protein Is a Key Molecule Regulation Mucin Secretion by Human Airway Epithelial Cells in Vitro*, The Journal of Biological Chemistry, vol. 276, No. 44, Nov. 2, 2001, pp. 40982–40990.
Li et al., *tsg101: A Novel Tumor Susceptibility Gene Isolated by Controlled Homozygous Functional Knockout of Allelic Loci in Mammalian Cells*, Cell, vol. 85, No. 3, May 3, 1996, pp. 319–329.
Prescott et al, *Chronic Mucus Hypersecretion in COPD and Death From Pulmonary Infection*, Eur. Respir. J., vol. 8, 1995, pp. 1333–1338.

(Continued)

Primary Examiner—Terry McKelvey
Assistant Examiner—Nancy T. Vogel
(74) Attorney, Agent, or Firm—Myers Bigel Sibley & Sajovec, P.A.

(57) ABSTRACT

Cultured mouse tracheal epithelial are grown in an air/liquid interface culture that allows them to develop differentiated characteristics (i.e., to develop into mucus cells or ciliated cells). This invention may be used for the growth of cells isolated from knockout and transgenic mice. The primary culture cells of the culture may be ciliated or non-ciliated differentiated cells.

13 Claims, 3 Drawing Sheets

OTHER PUBLICATIONS

Robinson et al., *Culture of Conducting Airway Epithelial Cells in Serum–Free Medium*, Journal of Tissue Culture Methods, vol. 13, 1991, pp. 95–102.

Steiger et al., *Concurrent Increases in the Storage and Release of Mucin–Like Molecules by Rat Airway Epithelial Cells in Response to Bacterial Endotoxin*, Am. J. Respir. Cell Mol. Biol, vol. 12, 1995, pp. 307–314.

Thornton et al., *Identification of Two Glycoforms of the MUC5B Mucin in Human Respiratory Mucus*, The Journal of Biological Chemistry, vol. 272, No. 14, Apr. 4, 1997, pp. 9561–9566.

Venglarik et al., *Oxygen Promotes CFTR Maturation and Trafficking in Mouse Tracheal Epithelial Cells*, FASEB Journal, Mar. 8, 2001, vol. 15, No. 5, pp. A848.

* cited by examiner

CULTURE SYSTEM FOR MOUSE TRACHEAL EPITHELIAL CELLS

CROSS REFERENCE TO RELATED APPLICATION

The present application claims priority to U.S. Provisional Application No. 60/287,638, filed Apr. 30, 2001, the disclosure of which is incorporated herein by reference in its entirety.

STATEMENT OF FEDERAL SUPPORT

This invention was made with support from the United States Federal government under grant numbers HL 36982 and HL 66236 from the Heart, Lung and Blood Institute of the National Institutes of Health. The United States government may have certain rights in this invention.

FIELD OF THE INVENTION

This invention relates to cell culture systems for mouse airway epithelial cells as well as methods for producing cell cultures from mouse epithelial cells.

BACKGROUND OF THE INVENTION

Early stage development of pharmaceuticals, including drug discovery and screening, relies heavily on the use of cultured cell lines. Cell lines are used, for example, to test putative drug therapies in cells intended to mimic a normal or diseased state of an organism to be treated. With regard to respiratory diseases, one shortcoming of known cell lines is that the cultured cells may have characteristics that are very different from the actual cells (e.g., epithelial cells) that are found in vivo during an active disease state.

To address this issue, differentiated primary cell cultures have been used to mimic in vivo-like cellular characteristics. See, e.g., T. M. Krunkosky et al., *Am. J. Respir. Cell. Mol. Biol.* 22, 685–692 (2000) (normal human bronchial epithelial, "NHBE" cells). U.S. Pat. No. 5,364,785 to Mather et al. describes a clonal cell line with a single epithelial cell type that has characteristics of bronchial or bronchiolar epithelial cells. Unfortunately, these primary cells can be difficult to manipulate due to their low efficiency of transferability.

Other methods have established tracheo-bronchial epithelial cell lines that maintain their differentiated function in vitro by relying on viral transformation or immortalization by transfection with various oncogenes. For example, U.S. Pat. No. 4,885,238, issued to Reddel et al., discloses human bronchial epithelial cells capable of growth in culture after viral transformation. These cells were transformed with SV40 or adenovirus-12 SV40 hybrid virus, or with a recombinant plasmid containing portions of the Rous sarcoma virus. The use of viruses to alter cellular function can be disadvantageous, as viral infection per se affects epithelial cells, thus creating cells that are not the same as those normally present in the organism being studied.

Certain known differentiated mouse epithelial cell culture systems require a feeder layer of another cell type. For example, mouse tracheal epithelial cells have been grown in an air/liquid interface culture on top of a collagen gel on a semi-permeable membrane, with the entire membrane co-cultured over a layer of NIH3T3 fibroblasts. H. Chen et al., *Respir. Crit. Care Med.* 161, A150 (2000). These feeder cells are frequently altered in some way, and, thus, do not mimic other primary cell types that might be present in the airway in vivo. Other systems comprise mouse airway epithelial cells that are grown in a less-differentiated state. For example, mouse tracheal epithelial cells have been grown submerged on plastic in an undifferentiated state. C. B. Robinson and R. Wu, *J. Tiss. Cult. Meth.* 13, 95–102 (1991). However, such systems are not optimal for testing potential drug therapies that will be used in cells that are highly differentiated in vivo.

Davidson et al. have disclosed a primary culture model of differentiated murine tracheal epithelial cells. See, D. J. Davidson et al., *Am. J. Physiol. Lung. Cell. Mol. Physiol.* 279, L766–L778 (2000). However, the presence of functional mucus cells was not observed in the transmission electron microscopy studies described in the initial report of the system. Moreover, the culture system appears to be limited to only one embodiment in which the result is a single culture morphology favoring ciliary cell development. It would be more advantageous to have a system that may be achieved by more than one method and by which a number of cell morphologies could be produced, such as mucus-secreting cells. Finally, the Davidson et al. technique utilizes a serum substitute in place of serum. A more advantageous method would be free of both serum and serum substitutes, thus providing a more simple method by which to study, for example, signal transduction in the cultured cells.

A significant challenge faced by researchers in respiratory diseases is correlating results from animal cell culture experiments to human trials. One intermediate method presently available for moving a potential drug/therapy from cell culture to human trial is through use of xenograft systems. See, e.g., U.S. Pat. No. 5,667,766 to Wilson et al., which disclosure is incorporated by reference herein in its entirety. However, these xenograft systems do not accurately mimic either in vitro or in vivo situations. A need still remains for a system that will reliably and accurately translate results from animal cell culture studies to human applicability.

Another area of study for researchers in respiratory diseases are mucins. Mucins are a family of glycoproteins secreted by the epithelial cells including those at the respiratory, gastrointestinal and female reproductive tracts. Mucins are responsible for the viscoelastic properties of mucus and at least eight mucin genes are known. D. J. Thornton, et al., *J. Biol. Chem.* 272, 9561–9566 (1997). Mucociliary impairment caused by mucin hypersecretion and/or mucus cell hyperplasia leads to airway mucus plugging that promotes chronic infection, airflow obstruction and sometimes death. Many airway diseases such chronic bronchitis, chronic obstructive pulmonary disease, bronchiectacis, asthma, cystic fibrosis and bacterial infections are characterized by mucin overproduction. E. Prescott, et al., *Eur. Respir. J.*, 8:1333–1338 (1995); K. C. Kim, et al., *Eur. Respir. J.*, 10:1438 (1997); D. Steiger, et al. *Am. J. Respir. Cell Mol. Biol.*, 12:307–314 (1995). Analysis of airway secretions has identified MUC5AC and MUC5B as the primary mucin constituents of the respiratory mucus gel. Generally, mucus hypersecretion/mucus cell hyperplasia is treated in two ways: physical methods to increase clearance and mucolytic agents. However, a need remains for agents and methods for reducing mucin production and treating the disorders associated with mucin hypersecretion. Therefore, systems and methods to screen compounds and treatments for mucus hypersecretion and related disorders are needed.

SUMMARY OF THE INVENTION

The present invention relates to cultured cells referred to herein as Mouse Tracheal Epithelial (MTE) cells. In one aspect, the invention relates to a new process wherein primary tracheal epithelial cells isolated from mouse airways are grown in an air/liquid interface culture that allows them to develop differentiated characteristics (i.e., to develop into mucus cells or ciliated cells). This invention may advantageously be used for the growth of cells isolated from knockout and transgenic mice. The present MTE cell culture system has been found to produce mucus as these cells can be noted histologically and the Mucin5AC protein has been detected from total intracellular protein from an MTE cell culture via Western analysis. The MTE cells also respond to known secretagogues by secreting mucin, i.e., are functional mucus cells.

The inventive methods of the present invention may provide advantages over known processes that allow growth of normal human bronchial epithelial cells in air/liquid interface culture. The new methods may also improve upon processes wherein mouse airway epithelial cells are grown in a less differentiated state, grown with fewer cell types present in a single culture, or co-cultured with feeder layers of non-epithelial cell types.

The MTE cell culture system of the present invention is a primary cell culture system that mimics in vivo epithelial cell characteristics, and may also allows use of cells from mice whose genetics/function has already been altered (i.e., knockout or transgenic animals). In addition, cells can be taken from in vivo mouse models of disease, so rapid in vitro screening techniques can be utilized on cells with disease-like characteristics.

The inventive MTE cell culture system is useftl for the study of signal transduction pathways, especially those controlling differentiation of epithelial cell types (ciliated and mucus). The system is also useful for the functional study of mucus cells, particularly their role in processes of importance to inflammatory airway disease such as mucus hypersecretion and mucus cell hyperplasia. The MTE cell cultures proliferate in response to interleukin 13, an inflammatory mediator shown to mediate epithelial cell proliferation during the development of a mucous-cell hyperplastic phenotype in human bronchial epithelial cell cultures (Booth et al., *Am. J. Respir. Cell Mol. Biol.* 25:739–743 (2001)). The new system also allows the study of signal transduction pathways without the confounding effects of serum, because the cell culture system has functionality with regard to mucus secretion in the absence of serum or serum substitute. This feature of the invention facilitates straightforward interpretation of cell signaling studies.

The present invention may be achieved and practiced in numerous embodiments, as described herein. In certain embodiments of the invention, the cell culture favors the development of ciliated cells, while others do not. Thus, the present invention permits comparisons between ciliated and non-ciliated (possibly mucus cell-dominated cultures).

The MTE culture system also provides a route for bringing potential drugs to clinical trials. Animal models of inflammatory respiratory disease such as the allergic asthmatic mouse model can be used to test new drugs, while airway epithelial cells taken from these animals can then be used for further testing and compared with the comparable human airway epithelial cell culture systems currently available. Thus, observations made during in vivo mouse trials can be explored further using the inventive MTE cell culture system, and results can be compared directly in the human cell culture system to determine whether the observed effect is generalized or species specific. In this manner, potential differences in results between animal and human models may be discovered prior to human clinical trials. This approach should aid in the process of development, screening, and testing of drugs and therapies that affect pathogenic processes of the upper airway such as mucus hypersecretion and mucus cell hyperplasia (e.g., goblet cell hyperplasia).

The foregoing and other aspects of the present invention are explained in detail in the specification set forth below.

BRIEF DESCRIPTION OF THE DRAWINGS

FIG. 2B depicts the control culture that was only exposed to the normal media required for MTE cell growth, while FIG. 2A depicts the IL-13-treated culture which was exposed to recombinant murine IL-13 (10ng/ml) for 9 days. The increase in epithelial cell number observed in the IL-13-treated culture indicates the ability of the MTE cell cultures to respond to molecules shown to be important for airway epithelial cell proliferation and mucous-cell hyperplasia development.

DETAILED DESCRIPTION OF THE PREFERED EMBODIMENTS

Figure 1:
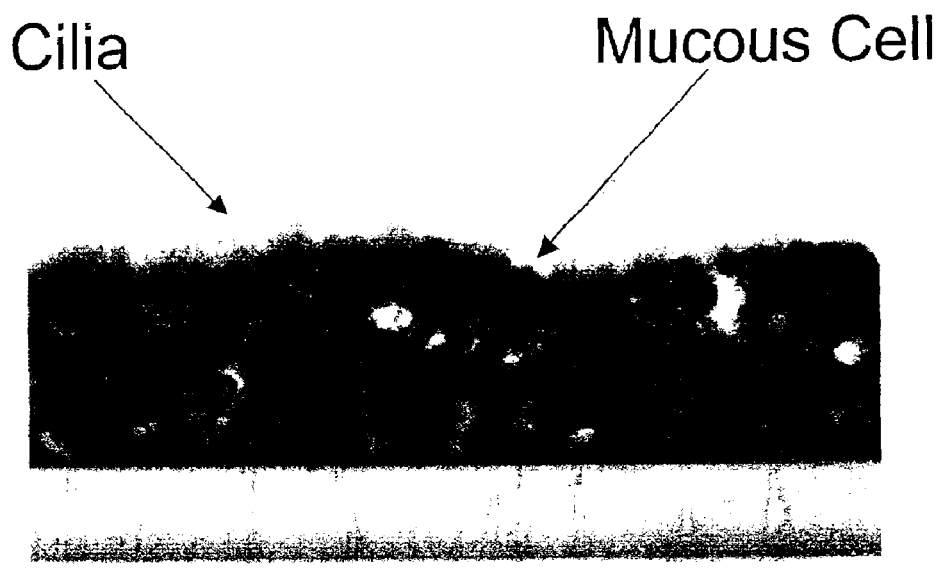
FIG. 1 is a photograph of a toluidine blue-stained cross-section of a murine tracheal epithelial cell (MTE) culture. Murine tracheal epithelial cells were grown in an air/liquid interface culture system. The stain shows the presence of cilia on the apical surface of many of the cells (indicated by "CILIA") as well as a darkly stained mucus cell (indicated as "MUCUS").

The present invention will now be described more fully hereinafter with reference to the accompanying figures, in which preferred embodiments of the invention are illustrated. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

As used herein, the term "airway" includes any of the air-containing tubes of an animal respiratory system. It includes, without limitation, the trachea, the bronchi, and the bronchioles. In a preferred embodiment, the airway is the trachea. Airway cells may be normal or diseased, and may be transformed or not transformed. Airway cells may be isolated from a healthy airway and subsequently altered in vitro, either transiently or genetically (e.g. by mutation or transfection or transformation with foreign DNA or other agents), or through chemical manipulation (i.e. treatment with a cytokine or growth factor) to a diseased cell. Airway cells may be isolated from a transgenic or knockout animal (e.g., a knockout mouse). In a preferred embodiment of the invention, the airways cells are rodent cells. In a more preferred embodiment, they are murine (mouse) cells.

Airway cells may be obtained by any means known in the art. In one embodiment, a trachea is removed from a sacrificed mouse, and cells are isolated from the removed trachea. The cells may be removed from the trachea by, for example, scraping the trachea with a suitable implement. Those skilled in the art will understand that tracheal cells may be treated with enzymes and/or other compounds, and/or subjected to known procedures (e.g., washing, centrifugation), in order to remove non-epithelial cells. In order to increase the number of isolated airway cells used to establish the cell culture, and thus decrease the number of animals that must be used to obtain the cells, the cells may be removed from the trachea and then grown initially in medium that comprises at least one growth factor (e.g., epidermal growth factor).

In one embodiment of the invention, isolated tracheal epithelial cells are seeded onto a solid support, which may be placed in a suitable culture chamber or vessel. The culture chamber may be, for example, a single well in a multi-well culture plate, which culture plates are known in the art. The well itself may be divided into more than one chamber (e.g., a basolateral chamber and an apical chamber).

In one embodiment, the solid support is a semi-permeable synthetic membrane, such as, for example, a Transwell-Clear® culture insert made by Corning CoStar. In a preferred embodiment, one side of the support membrane is exposed to a basolateral medium (i.e., is exposed to basolateral medium contained in a basolateral chamber of a culture well), while the second side of the support is exposed to an apical medium (i.e., is exposed to apical medium contained in an apical chamber of a culture well). In this embodiment, cells isolated from the mouse trachea are seeded onto apical side of the support, with both the apical and basolateral sides of the support being exposed to culture medium.

The basolateral and apical media may be different from each other, or may be the same. In a preferred embodiment, the basolateral and apical media are growth media comprising, for example, Dulbecco's Modification of Eagle's Medium/Ham's F-12 (DMEM F-12, Invitrogen Corporation, Carlsbad, Calif.). The growth media may optionally contain media additives that can be selected by one skilled in the art. Additives include but are not limited to one or more of amphotericin, gentamicin, bovine pituitary extract (BPE), insulin, transferrin, epidermal growth factor (EGF) (either human or murine), dexamethasone, cholera toxin, and retinal acetate. In one embodiment, the basolateral media may additionally comprise serum (e.g., fetal calf serum), in a concentration that may be determined by the skilled artisan to be suitable (e.g., 5%, or 10%, or 15% or 20% or another percentage determined by the practitioner). Additionally serum substitutes known in the art may be used.

Cells seeded onto the support are incubated under conditions (e.g., temperature, atmosphere, gently agitating) suitable to initiate the cell culture. The length of time for incubation may be determined by the skilled artisan, but will preferably be at least one day, more preferably at least two days, and even more preferably at least four days. In one preferred embodiment, the cells are incubated for five days. As stated above, during this initial phase the media used is serum.

After the initial incubation, the apical medium is removed (e.g., is removed from the apical chamber to which the apical side of the solid support is exposed) in order to create an air-liquid interface. The cells are then maintained at the air-liquid interface. The cells grown at the air-liquid interface remain differentiated. For example, the cells are maintained in a differentiated state for a length of time for more than two days. In another embodiment the cells are maintained in a differentiated state for a length of time for more than five days. In yet another embodiment, the cells are maintained in a differentiated state for a length of time for more than ten days. In still another embodiment the cells are maintained in a differentiated state for a length of time for more than fifteen days. In a preferred embodiment, the cells are maintained in a differentiated state for sixteen days. As defined herein "differentiation" includes both entry into a specific lineage pathway and functional activation of differentiated cells.

The basolateral medium may be replaced at intervals that may be determined by the practitioner. In one embodiment of the invention, the basolateral medium comprises serum (e.g., fetal calf serum) during initial incubation (ie., before the air-liquid interface is created) and after the air-liquid interface is created. For example, the basolateral medium may comprise serum during the entire life of the culture. The basolateral medium may comprise 5% to 10% serum, or any other percentage deemed suitable by the practitioner. In other embodiments, the 5% to 10% fetal calf serum is present in the basolateral compartment of the culture well only during the first 24 hours of growth. In this embodiment, no additional serum is used for the remainder of the incubation and culture period. In another embodiment, the basolateral medium comprises 5% to 10% serum until the air/liquid interface is established (i.e., during the initial incubation).

The MTE cell culture produced by the methods of the present invention may comprise ciliated cells and non-ciliated cells. The MTE cells produced by the present invention may also comprise mucus-producing cells (e.g., goblet cells). In one embodiment, the culture comprises both ciliated cells and non-ciliated cells. In another embodiment, the culture comprises predominantly ciliated cells. In still another embodiment, the culture comprises predominantly non-ciliated cells. In another embodiment, the culture consists essentially of ciliated cells. In another embodiment, the culture consists essentially of non-ciliated cells.

In another embodiment of the invention, tracheal epithelial cells to be cultured using the system are isolated from transgenic animals or knockout animals. Transgenic animals are animals that have had genes from another organism put into its genome through recombinant DNA techniques. The transgenic animals may have a partial loss of function in one or both alleles of an endogenous gene. Alternatively, the transgenic animals may have an introduced transgene with altered genetic sequence and/or function from an endogenous gene. In the present invention, knockout animals are animals in which the function of a particular gene has been completely eliminated. In certain embodiments of the invention, epithelial cells may be taken from either the transgenic or knockout animals. In particular embodiments of the invention, the cells taken from the transgenic animal or knockout animal that overproduce mucin and/or mucus. Epithelial cells may also be isolated from the transgenic or knockout animals.

In a knockout animal, the target gene expression is preferably undetectable or insignificant (e.g., less than 20%, preferably below 10%, and even more preferably below 5%). This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence.

Different methods may be used to achieve the "knockout". A chromosomal deletion of all or part of the native gene may be induced, including deletions of the non-coding regions, particularly the promoter region, 3' regulatory sequences, enhancers, or deletions of gene that activate expression of target genes. A functional knockout may also be achieved by the introduction of an anti-sense construct that blocks expression of the native genes (for example, see Li and Cohen, Cell 85, 319–329 (1996)).

"Knockouts" also include conditional knockouts, for example where alteration of the target gene occurs upon exposure of the animal to a substance that promotes target gene alteration, introduction of an enzyme that promotes recombination at the target gene site, or other method for directing the target gene alteration postnatally.

The invention may be useful for comparing the effects of drugs or therapies on epithelial cells with various gene functions eliminated or over-expressed through comparing cultures from wild-type and knockout or transgenic mice. The present invention may also provide an additional step in the process of screening pharmaceuticals prior to human testing, by allowing a comparison between in vivo effects in animal disease models and in vitro cell culture systems. As a human airway epithelial cell culture system has already been established, the MTE cell culture system may also be used as a way to compare effects observed in human cells with effects in mouse cells prior to using mouse models for animal testing. Alternatively, any ill effects observed in animal trials could be examined further in the MTE cell system so the potentially harmful effects could be examined effectively in the human in vitro cell culture system. With either approach, it is anticipated that this new cell culture system will aid in the ability to compare the effects of therapeutics in animal models to potential effects in humans.

The MTE cell culture can also be readily applied to in vitro studies of a variety of airway epithelial cell functions that may be of importance in respiratory disease. As with the human bronchial epithelial cell cultures, the MTE cell cultures retain primary cell characteristics similar to or identical to those observed in vivo. However, in contrast to the human cells, the use of transgenic and knockout animals as a source of the MTE cells allows examination of cellular processes in an altered genetic/functional state.

The invention may also be useful as a model to assay the effect of various agents and therapies, particularly the efficacy or toxicity of therapeutic and other agents, methods, and compositions, that may be used to treat lung disease, particularly mucus-cell hyperplasia and mucus hypersecretion, in humans or animals. One of the embodiments of the present invention provides methods to study the delivery, mechanism of action, effectiveness or toxicity of therapeutic agents for lung disease. The method of this embodiment may comprise the step of introducing the therapeutic agent to the MTE culture and then assessing the effect of the agent on the cells of the culture. For example, cells cultured according to the invention may be exposed to agents that may affect the uptake of sodium ions by the respiratory epithelium, or other agents that may affect viscosity, secretion or clearance of mucus. Additionally, the efficacy or toxicity of gene therapy for lung disease may be assessed by exposing the MTE cells of this invention to recombinant viruses, liposomes, DNA-protein complexes or other vehicles carrying foreign DNA. After uptake of the DNA by the cells of the invention, the cells can be studied, to determine the amount, the cell-specific location and the effect of the gene therapy on the cells and the disease state.

In yet another embodiment of this invention, cells grown by the method of this invention may be exposed to agents that are known to complicate the course of a lung disease. For example, the cells of this invention may be exposed to *Pneumococcus*, *Pseudomonas* and other infective agents. The effect of selected agents (e.g., putative drugs) on the diseased airway may then be compared to their effect on non-infected cells in order to assess the differences in the physiological response to such agents.

In another embodiment of this invention, cells of the present invention may be exposed to various agents, such as environmental agents, potential toxins, and cigarette smoke, in order to study the potential effect of those agents on lungs. Such airways may also be used to assess the ability of various therapies and treatments to avoid or lessen the effects, if any, of such toxins and agents.

In another embodiment of the present invention, inflammatory mediators such as IL-13 may be added. The introduction of such inflammatory mediators may result in the proliferation of human airway epithelial cells in vitro. See, Booth et al., supra. Thus, there may be an increase in the number of mucus producing cells. This illustrates the ability of MTE cultures to respond to mucus cell hyperplasic and proliferative important mediators. It additionally illustrates the ability to use the cultures from above to study mucus cell hyperplasia and epithelial cell hypertrophy.

In order that this invention may be better understood, the following examples are set forth. These examples are for purposes of illustration only, and are not to be construed as limiting the scope of the invention in any manner.

EXAMPLE 1

Isolation of Murine Tracheal Epithelial (MTE) Cells From Mice Trachea

To assist in the isolation of murine tracheal epithelial cells from mice trachea, mice were sacrificed via cervical dislocation, and trachea removed. The trachea were then submerged in a solution of 0.01% pronase (Sigma, St. Louis, Mo.) in Ham's F12 medium, and incubated for 1 hour at 37° C. The trachea was opened longitudinally to permit the solution of pronase to infuse the tissue. Following incubation in pronase, the trachea was scraped gently and the epithelial cells were collected by centrifugation (500Xg, 4° C., 10 min). Cells were then resuspended in 5 ml of DMEM F12 growth medium, plus additives (see table 1 below.)

TABLE 1

Additives to growth medium.

| Supplement | Final Concentration |
| --- | --- |
| Amphotericin | 250 µg/ml |
| Nystatin | 20 U/ml |
| Gentamicin | 50 µg/ml |
| Bovine Pituitary Extract (BPE) | 104 µg/ml |
| Insulin | 5 µg/ml |
| Transferrin | 5 µg/ml |
| Epidermal Growth Factor (EGF) | 6.25 to 25 ng/ml |
| Dexamethasone | 0.1 µM |
| Cholera Toxin | 20 ng/ml |
| Retinal Acetate | $1 \times 10^{-8}$ M |
| Fetal Calf Serum* | 10% |

*Placed for the first 24 hours in the basolateral compartment of the culture insert.

EXAMPLE 2

Cell Culture

The tracheal epithelial cells isolated in Example 1 were grown on transparent, semi-permeable polyester membrane culture inserts (Transwell-Clear®, 24.5 mm, 0.45 µm pore size, Corning Costar), as is known in the art. Prior to seeding with cells, these membranes were thin-coated with 300 µg/ml rat tail collagen, type 1 (Collaborative Biomedical Products) in 0.02N glacial acetic acid and equilibrated for 60 minutes at room temperature. The membranes were then washed in phosphate buffered saline containing nystatin and gentamicin (see above table), and conditioned for two hours to overnight at 37° C. by adding a minimal medium (such as DMEM F12) containing nystatin and gentamicin to the basolateral compartment.

Epithelial cells isolated from the trachea of two mice were used to seed a one $cm^2$ area. Cells were placed in the apical chamber of the culture insert in medium comprising DMEM F12 plus additives (see above table). The basolateral chamber was supplied with medium and 10% FCS for 24 hours, after which FCS was no longer added to the basolateral media. Cells were maintained for 5 days and then the apical media was removed to create an air/liquid interface. Cells were then maintained in culture for approximately 16 more days.

FIG. 1 is a photograph of a toluidine blue-stained cross-section of a murine tracheal epithelial cell culture. Murine tracheal epithelial cells were grown in an airliquid interface culture system as described above. The stain shows the presence of cilia on the apical surface of many of the cells (indicated by "CILIA") as well as a darkly stained mucus cell (indicated as "MUCUS").

EXAMPLE 3

Alternative Embodiments of MTE System

The MTE cell cultures described above may be achieved using several alternative embodiments of the invention. In one embodiment of the invention, 10% fetal calf serum is present in the basolateral compartment of the culture well only during the first 24 hours of growth. In this embodiment, no additional serum was used for the remainder of the culture period. In another embodiment, 10% serum top and bottom were used for the first 24 hours of growth, with no additional use of serum. This is referred to as "Method 1—No FCS."

Figure 2A:
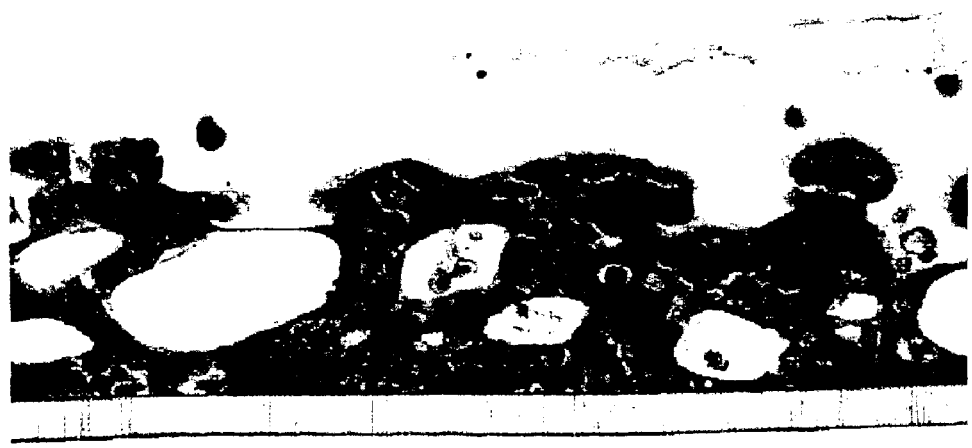
FIGS. 2A and 2B includes two photographs of Periodic Acid Schiff-stained cross-sections of MTE cell cultures.
Figure 2B:

The present methods were also used to achieve MTE cultures grown with 5% serum until the air/liquid interface is established. This is referred to as "Method 2—Combination." This approach allows for more rapid growth of the cells while removing the confounding effects of serum for the experimentation period. Additionally, Method 2 cultures have been shown to respond to IL-13 with proliferation. FIGS. 2A and 2B illustrate the increase in the epithelial cell number of cell cultures exposed to an IL-13 regimen. Specifically FIGS. 2A and 2B show two photographs of Periodic Acid Schiff-stained cross-sections of MTE cell cultures. FIG. 2A depicts an IL-13-treated culture that was exposed to recombinant murine IL-13 (10ng/ml) for 9 days while FIG. 2B is a photograph of a control culture that was only exposed to the normal media required for MTE cell growth. The increase in epithelial cell number observed in the IL-13-treated culture indicates that the ability of the MTE cell cultures to respond to the molecules shown may be advantageous for airway epithelial cell proliferation and mucous-cell hyperplasia development.

In the "Method 3—FCS Only," embodiment of the invention, cells were grown continually in the presence of 5% serum. Mucin secretion has been confirmed in "Method 1" cultures, but the other methods appear to have mucus cells as noted via histology. Scanning electron microscopy reveals that the "Method 3—FCS Only" cultures have ciliated cells.

EXAMPLE 4

Role of MTE Cell Cultures in Drug Testing and Clinical Trials

Figure 3:
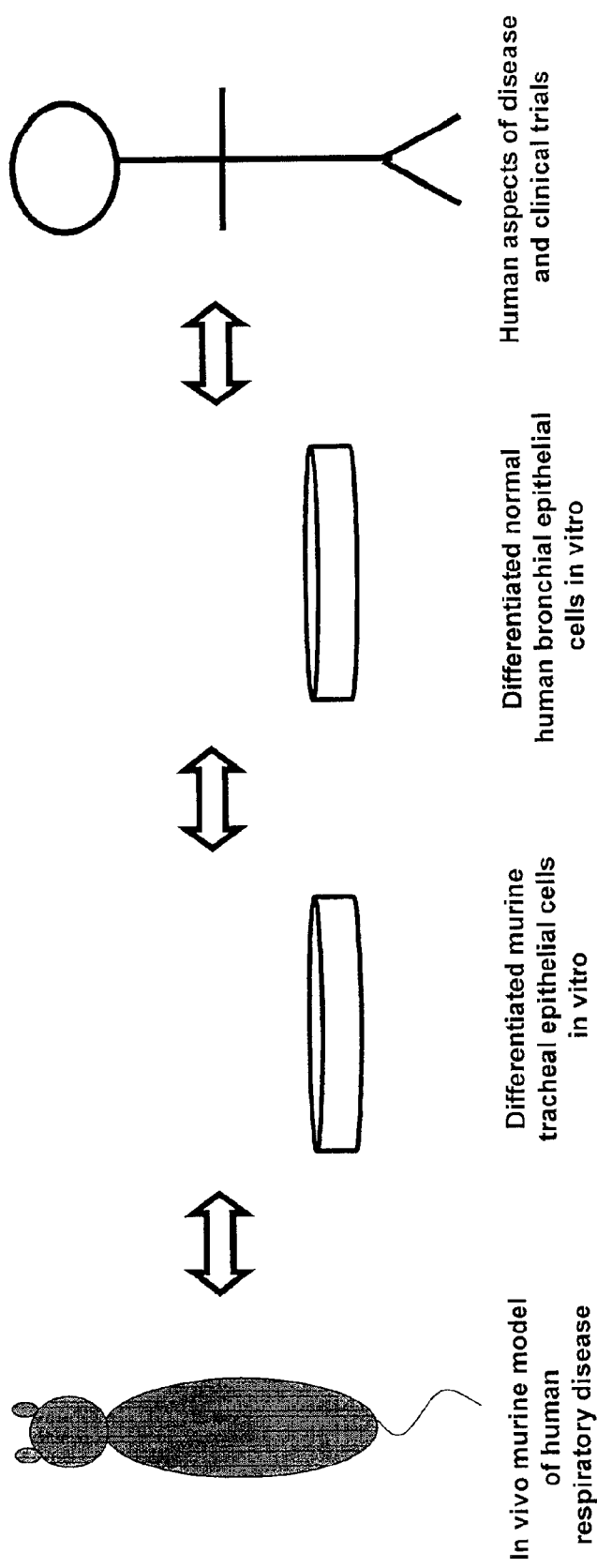
FIG. 3 is a graphical representation of an embodiment of the invention wherein MTE cells are used in drug testing and/or clinical trials.

Effects exhibited in murine models of human respiratory disease during drug testing can be compared with the newly developed MTE cell culture system of the present invention. This technique allows for the direct comparison with a previously developed human primary cell culture system (NHBE cells). (Krunkosky et al., *Am J Respir Cell Mol Biol* 2:1–8, (2000)). From such an examination, one may determine whether observed effects can be generalized or are-species specific. Thus, information gleaned via this process can be applied to the development of appropriate clinical human trials. This is demonstrated in FIG. 3, which depicts a graphical representation of an embodiment of the present invention wherein MTE cells may be used in drug testing and/or clinical trials. For example, the effects seen in murine models of human respiratory disease during drug testing can be compared with the newly developed MTE cell culture system. This will allow direct comparisons with a previously developed human primary cell culture system (NHBE cells). From such an examination, it should be possible to determine whether observed effects can be generalized or are species specific. Thus, information gleaned via this process can be applied to the development of appropriate clinical human trials.

The foregoing examples are illustrative of the present invention and are not to be construed as limiting thereof. The invention is defined by the following claims, with equivalents of the claims to be included therein.

What is claimed is:

1. A method for producing a culture of differentiated, mouse airway epithelial cells comprising at least 5% mucus cells comprising:

obtaining tracheal epithelial cells from a mouse; and then maintaining the cells at an air-liquid interface to produce a culture of mouse airway epithelial cells comprising at least 5% mucus cells, whereby the cells remain differentiated.

2. The method according to claim 1, whereby the maintenance step comprises:

growing the tracheal epithelial cells on a solid support, wherein a first side of the support is in contact with a basolateral medium, and a second side of the support is in contact with an apical medium;

removing the apical medium to create the air-liquid interface; and continuing to grow the epithelial cells at the air-liquid interface.

3. The method according to claim 2, wherein the solid support is a semi-permeable membrane.

4. The method according to claim 2, wherein the basolateral medium comprises serum.

5. The method according to claim 2, wherein the basolateral medium comprises 5% to 10% serum.

6. The method according to claim 2, wherein the basolateral medium comprises serum until the air-liquid interface is created.

7. The method according to claim 1, wherein the mouse is a transgenic mouse.

8. The method according to claim 1, wherein the mouse is a knockout mouse.

9. The method according to claim 1, wherein the tracheal epithelial cells produce mucin.

10. The method according to claim 1, wherein the culture further comprises ciliated cells.

11. The method according to claim 1, wherein the culture further comprises goblet cells.

12. The method according to claim 1, wherein the tracheal epithelial cells proliferate in response to an inflammatory mediator.

13. The method according to claim 12, wherein said inflammatory mediator is IL-13.

* * * * *